US00PP22418P2

(12) United States Plant Patent
Kaagman

(10) Patent No.: US PP22,418 P2
(45) Date of Patent: Dec. 27, 2011

(54) *OSTEOSPERMUM* PLANT NAMED 'TRA YEL'

(50) Latin Name: *Osteospermum ecklonis*
Varietal Denomination: Tra Yel

(75) Inventor: Pim Kaagman, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 204 days.

(21) Appl. No.: 12/657,456

(22) Filed: Jan. 21, 2010

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

| | | | | |
|---|---|---|---|---|
| PP18,517 | P2 * | 2/2008 | Klemm | Plt./360 |
| PP20,332 | P2 * | 9/2009 | Sekiguchi et al. | Plt./360 |
| PP21,344 | P2 * | 9/2010 | Barends | Plt./360 |

OTHER PUBLICATIONS

UPOV ROM GTITM Jouve Retrieval Software 2011/01 Citation for 'Tra Yel' (Tradename: "Tradewinds Yellow").*

* cited by examiner

*Primary Examiner* — Wendy C Haas
(74) *Attorney, Agent, or Firm* — S. Matthew Edwards

(57) ABSTRACT

A new *Osteospermum* plant named 'Tra Yel' particularly distinguished by the medium to large yellow ray florets, early flowering habit, compact and upright plant habit with slightly yellow-green leaves and excellent branching.

1 Drawing Sheet

Latin name of the genus and species of the plant claimed: *Osteospermum ecklonis*.

Varietal denomination: 'Tra Yel'.

BACKGROUND OF THE NEW PLANT

The present invention comprises a new *Osteospermum*, botanically known as *Osteospermum ecklonis*, and hereinafter referred to by the variety name 'Tra Yel.'

'Tra Yel' is a product of a planned breeding program. The new cultivar has medium to large yellow ray florets, early flowering habit, compact and upright plant habit with slightly yellow-green leaves and excellent branching.

'Tra Yel' originated from a hybridization made in July 2006 in a controlled breeding environment in Andijk, Netherlands. The seed was sown in September 2006.

The female parent was the proprietary plant designated 'O04-223-1,' unpatented, with cream and blue eyed flowers. 'O04-223-1' has less vigor and less compact plant than 'Tra Yel.'

The male parent of 'Tra Yel' was the proprietary plant designated as 'O04-214-3,' unpatented, with terracotta colored ray florets. 'O04-214-3' has less vigor and taller plant habit than 'Tra Yel.'

'Tra Yel' was selected as one flowering plant within the progeny of the stated cross in January 2007 in a controlled environment in Andijk, Netherlands.

The first act of asexual reproduction of 'Tra Yel' was accomplished when terminal cuttings were propagated from the initial selection in January 2007 in a controlled environment in Andijk, Netherlands.

BRIEF SUMMARY OF INVENTION

Horticultural examination of plants grown from cuttings of the plant initiated in January 2007, and continuing thereafter, has demonstrated that the combination of characteristics as herein disclosed for 'Tra Yel' are firmly fixed and are retained through successive generations of asexual reproduction.

'Tra Yel' has not been observed under all possible environmental conditions. The phenotype may vary significantly with variations in environment such as temperature, light intensity and day length.

A Plant Breeder's Right for this cultivar was applied for in Canada on Jan. 30, 2009. 'Tra Yel' has not been made publicly available more than one year prior to the filing of this application.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

The accompanying photographic drawing shows typical flower and foliage characteristics of 'Tra Yel' with colors being as true as possible with an illustration of this type.

Figure 1:
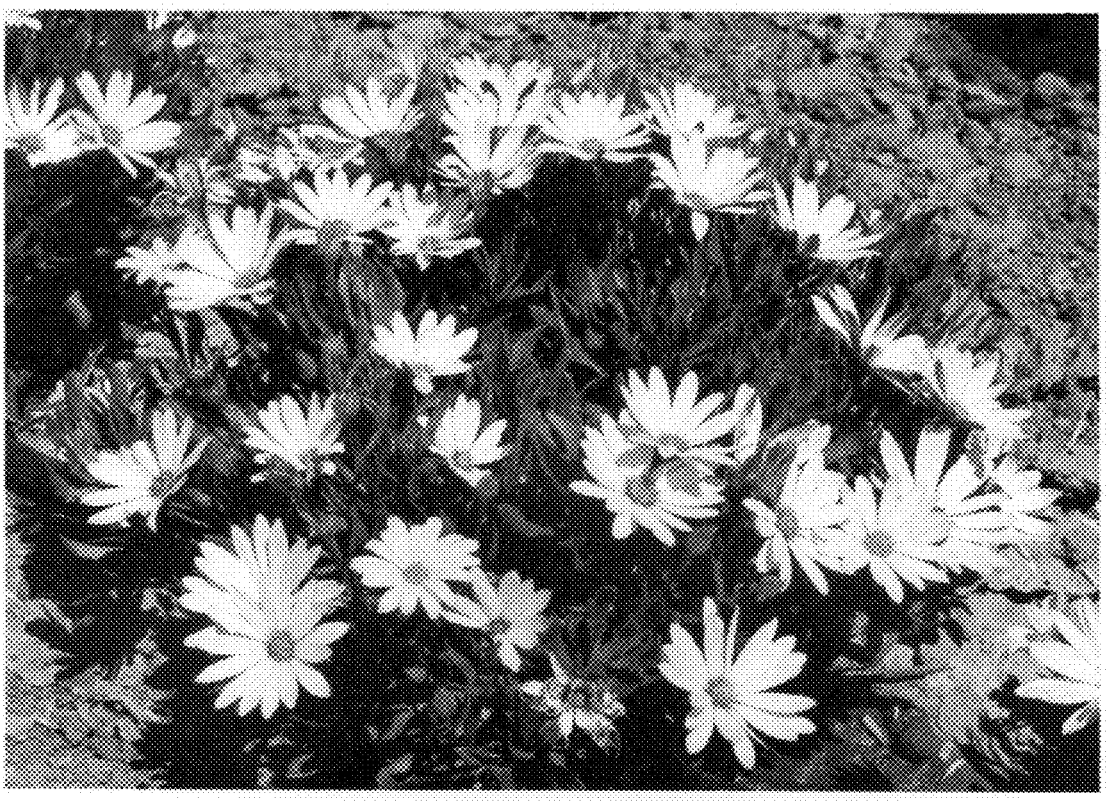
Figure 2:
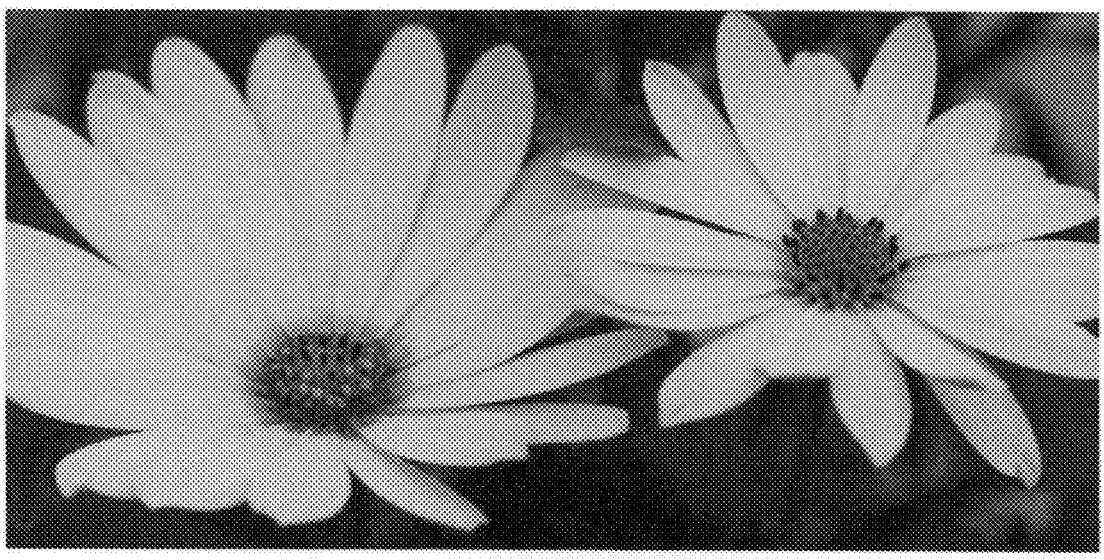

The photographic drawing shows in FIG. 1., a flowering plant of the new variety growing in a outdoor field trial in Gilroy, Calif. in the summer of 2009 and in FIG. 2., a close-up of the flowers. These plants are approximately 7-8 months of age.

DETAILED BOTANICAL DESCRIPTION

The plant descriptions and measurements were taken in late summer 2009 in Salinas, Calif. under natural light. These plants were started and grown in Gilroy, Calif., and then planted into an outdoor garden in Salinas. Plants were approximately 8-9 months old.

Color references are made to The Royal Horticultural Society Colour Chart (R.H.S.) 2001.

TABLE 1

DIFFERENCES BETWEEN THE NEW VARIETY 'TRA YEL' AND A SIMILAR VARIETY

| | 'Tra Yel' | KLE0E05524' (U.S. Plant Pat. No. 18,517) |
|---|---|---|
| Ray petal color: | RHS 10A | RHS 14A |
| Foliage length: | Shorter | Longer |
| Vigor: | More | Less |

Plant:

*Form, growth and habit.*—Compact, semi-upright and mounded plant habit. Vigorous habit.

*Plant height.*—About 40 cm.

*Plant height (inflorescence included).*—About 46 cm.

*Plant width.*—About 50-55 cm.

Garden performance and tolerance to weather.—Very good.

*Crop time to flowering.*—About 10 weeks.

Roots:

*Number of days to initiate and produce roots.*—24-27 days at about 22 degrees.

*Type.*—Fine, fibrous, free branching.

*Color.*—RHS N155B but whiter.

Foliage:

*Arrangement.*—Alternate.

*Immature, leaf color, upper surface.*—RHS 146B.

*Lower surface.*—Closest to RHS 146B.

*Mature, leaf color, upper surface.*—RHS 146A.

*Lower surface.*—Closest to RHS 146B.

*Length.*—4.3-5.0 cm.

*Width.*—1.1-2.1 cm.

*Shape.*—Broadly elliptical.

*Base shape.*—Attenuate.

*Apex shape.*—Acute.

*Margin.*—Slightly serrate.

*Texture, upper surface.*—Hirsute.

*Lower surface.*—Hirsute.

*Color of veins, upper surface.*—Indistinct.

*Color of veins, lower surface.*—Indistinct.

*Petiole color.*—RHS 146C.

*Length.*—1.3-1.6 cm.

*Diameter.*—0.25-0.3 cm.

*Texture.*—Hirsute.

Stem:

*Quantity of main branches per plant.*—5-6.

*Color of stem.*—Between RHS 144A and RHS 144B with slight anthocyanins in patches closest to RHS 176B.

*Length of stem.*—35-40 cm.

*Diameter.*—0.4 cm.

*Length of internodes.*—1.5-2.0 cm.

*Texture.*—Glabrous.

*Color of peduncle.*—Between RHS 144A and RHS 144B.

*Length of peduncle.*—12-15 cm.

*Peduncle diameter.*—0.2 cm.

*Texture.*—Hirsute and hispid.

Inflorescence:

*Type.*—Daisy-type inflorescence form, held above the foliage, arising from leaf axis. Disc and ray florets developing acropetally on a capitulum. Freely flowering habit, numerous inflorescences per plant develop over time.

*Quantity of inflorescences per plant.*—35-45.

*Lastingness of individual blooms on the plant.*—11-14 days.

*Fragrance.*—None.

Bud (just before opening/showing color):

*Color.*—RHS 1B with RHS 166B to RHS 166C in slight patches.

*Length.*—2.0-2.5 cm.

*Width.*—0.9-1.1 cm.

*Shape.*—Oblate.

Immature inflorescence:

*Diameter.*—4.0-4.5 cm.

*Color of ray florets, upper surface.*—RHS 12B but a little lighter.

*Lower surface.*—RHS 6C base color overlaid with RHS 165A in varying shades and mainly down the middle.

Mature inflorescence:

*Diameter.*—4.5-5.5 cm.

*Depth.*—2.0 cm.

*Total diameter of 'disc'.*—0.9-1.1 cm.

Ray florets:

*Average quantity of florets.*—14-18 in 1-2 whorls.

*Color of florets, upper surface.*—RHS 10A with RHS 176B basally.

*Lower surface.*—Closest to RHS 9B with varying hues of RHS 166A and RHS 165A down the middle.

*Length.*—2.8-3.0 cm.

*Width.*—0.6-0.7 cm.

*Shape.*—Elliptical.

*Apex shape.*—Praemorse.

*Margin.*—Entire.

*Texture, upper surface.*—Papillose.

*Lower surface.*—Papillose.

Disc florets:

*Average quantity of florets.*—About 55.

*Color of florets.*—About RHS 4D but lighter.

*Length.*—0.5-0.6 cm.

*Width.*—0.15 cm.

*Shape.*—Tubular, enlongated.

*Apex shape.*—Acute, 5 pointed.

Phyllaries:

*Quantity.*—14-15.

*Color, upper surface.*—RHS 146A.

*Lower surface.*—RHS 146A.

*Length.*—0.7-1.1 cm.

*Width.*—0.75-0.1 cm.

*Shape.*—Linear.

*Apex shape.*—Acute.

*Based.*—Fused.

*Margins.*—Entire.

*Texture, upper surface.*—Smooth.

*Lower surface.*—Scabrous and/or hirsute.

Reproductive organs:

*Gynoecium.*—Found on both florets.

*Pistil.*—1.

*Length.*—0.3 cm.

*Style color.*—About RHS 200A but more red.

*Style length.*—0.15-0.25 cm.

*Stigma color.*—About RHS 155D.

*Androecium.*—Found on only disc florets.

*Stamens.*—4-5.

*Color of filaments.*—RHS 155D.

*Length filaments.*—0.3 cm.

*Anther color.*—About RHS 200A but with more red.

*Anther length.*—0.4 cm.

*Anther shape.*—Oblong.

*Color of pollen.*—RHS 17B.

*Pollen amount.*—Abundant.

*Fertility/seed set.*—Has not been observed on this hybrid.

Disease/pest resistance: Disease/pest resistance has not been observed on this hybrid.

What is claimed is:

1. A new and distinct variety of *Osteospermum* plant named 'Tra Yel,' substantially as illustrated and described herein.

* * * * *